US006620846B1

(12) United States Patent
Jonn et al.

(10) Patent No.: US 6,620,846 B1
(45) Date of Patent: Sep. 16, 2003

(54) ABSORBABLE ADHESIVE COMPOSITIONS

(75) Inventors: Jerry Y. Jonn, Raleigh, NC (US); John Bobo, Raleigh, NC (US); Julian Quintero, Raleigh, NC (US); Jon P. Moseley, Raleigh, NC (US)

(73) Assignee: Closure Medical Corporation, Raleigh, NC (US)

( * ) Notice: Subject to any disclaimer, the term of this patent is extended or adjusted under 35 U.S.C. 154(b) by 0 days.

(21) Appl. No.: 09/630,437

(22) Filed: Aug. 2, 2000

(51) Int. Cl.$^7$ ........................ A61K 31/275; A01N 37/34
(52) U.S. Cl. ........................ 514/519; 424/451; 514/642; 514/644
(58) Field of Search ................ 424/443, 447, 424/451; 514/519, 642, 644

(56) References Cited

U.S. PATENT DOCUMENTS

| | | |
|---|---|---|
| 3,559,652 A | 2/1971 | Banitt .................. 128/334 |
| 3,903,055 A | 9/1975 | Buck |
| 3,940,362 A | 2/1976 | Overhults |
| 3,995,641 A | 12/1976 | Kronenthal et al. |
| 4,012,402 A | 3/1977 | Buck |
| 4,152,284 A | 5/1979 | Morlock et al. |
| 4,321,180 A | 3/1982 | Kimura et al. |
| 4,378,213 A | 3/1983 | Severy |
| 4,460,759 A | 7/1984 | Robins |
| 4,467,079 A | 8/1984 | Hechenberger et al. |
| 4,696,983 A | 9/1987 | Cohen |
| 4,702,783 A | 10/1987 | Mason, III |
| 4,713,235 A | 12/1987 | Krall |
| 4,793,886 A | 12/1988 | Okamura et al. |
| 4,837,286 A | 6/1989 | Kato et al. |
| 4,933,234 A | 6/1990 | Kobe et al. |
| 4,979,993 A | 12/1990 | Okamoto et al. |
| 4,981,483 A | 1/1991 | Akimova et al. ........... 606/214 |
| 5,045,614 A | 9/1991 | Buchholz et al. |
| 5,066,743 A | 11/1991 | Okamoto et al. |
| 5,079,098 A | 1/1992 | Liu |
| 5,154,320 A | 10/1992 | Bolduc |
| 5,194,537 A | 3/1993 | Bhaskaran et al. |
| 5,259,835 A | 11/1993 | Clark et al. |
| 5,262,200 A | 11/1993 | Puder et al. |
| 5,328,687 A | 7/1994 | Leung et al. |
| 5,344,902 A | 9/1994 | Harwood et al. |
| 5,445,597 A | 8/1995 | Clark et al. |
| 5,494,983 A | 2/1996 | Reetz et al. |
| 5,514,371 A | 5/1996 | Leung et al. |
| 5,514,372 A | 5/1996 | Leung et al. |
| 5,575,997 A | 11/1996 | Leung et al. |
| 5,582,834 A | 12/1996 | Leung et al. |
| 5,624,669 A | 4/1997 | Leung et al. |
| 5,902,443 A | 5/1999 | Kanakubo et al. |
| 5,928,611 A | 7/1999 | Leung |
| 5,981,621 A | 11/1999 | Clark et al. |
| 6,010,714 A | 1/2000 | Leung et al. |
| 6,055,828 A | 5/2000 | Rivera et al. |
| 6,283,933 B1 * | 9/2001 | D'Alessio et al. .......... 604/3 |

FOREIGN PATENT DOCUMENTS

| | | |
|---|---|---|
| EP | 0 374 252 | 6/1990 |
| EP | 0 965 623 | 12/1999 |
| WO | WO 97/31598 | 9/1997 |
| WO | WO 00/38777 | * 7/2000 |
| WO | WO 01/32319 A2 | 5/2001 |

OTHER PUBLICATIONS

Jaffe H et al., "Synthesis and bioevaluation of alkyl 2–cyanoacryloyl glycolates as potential soft tissue adhesives", Journal of Biomedical Materials Research, vol. 20, No. 2, 1096, pp. 205–212.

* cited by examiner

Primary Examiner—Jose' G. Dees
Assistant Examiner—Konata M. George
(74) Attorney, Agent, or Firm—Oliff & Berridge, PLC

(57) ABSTRACT

A method of treating living tissue includes applying to living tissue a biocompatible adhesive composition containing at least one alkyl ester cyanoacrylate monomer and a polymerization initiator or accelerator, wherein the polymerization initiator or accelerator is a quaternary amine.

72 Claims, No Drawings

ABSORBABLE ADHESIVE COMPOSITIONS

BACKGROUND OF THE INVENTION

1. Field of the Invention

The invention relates to monomer and polymer adhesive and sealant compositions, and to their production and use for industrial and medical applications.

2. State of the Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made α-cyanoacrylate adhesives the primary choice for numerous applications such as bonding plastics, rubbers, glass, metals, wood, and, more recently, biological tissues.

Medical applications of 1,1-disubstituted ethylene adhesive compositions include use as an alternate or an adjunct to surgical sutures and staples in wound closure as well as for covering and protecting surface wounds such as lacerations, abrasions, burns, stomatitis, sores, and other surface wounds. When an adhesive is applied, it is usually applied in its monomeric form, and the resultant polymerization gives rise to the desired adhesive bond.

For example, polymerizable 1,1-disubstituted ethylene monomers, and adhesive compositions comprising such monomers, are disclosed in U.S. Pat. No. 5,328,687 to Leung et al. Suitable methods for applying such compositions to substrates, and particularly in medical applications, are described in, for example, U.S. Pat. Nos. 5,928,611; 5,582,834; 5,575,997; and 5,624,669, all to Leung et al.

Some monomeric α-cyanoacrylates are extremely reactive, polymerizing rapidly in the presence of even minute amounts of an initiator, including moisture present in the air or on moist surfaces such as animal tissue. Monomers of α-cyanoacrylates are anionically polymerizable or free radical polymerizable, or polymerizable by zwitterions or ion pairs to form polymers. Once polymerization has been initiated, the cure rate can be very rapid to very slow, depending on the choice of monomer.

However, not all cyanoacrylates polymerize at the same rate; and therefore, various initiators have been added to cyanoacrylates to induce polymerization. For example, each of U.S. Pat. Nos. 5,928,611 to Leung; 5,902,443 to Kanakubo et al.; 4,460,759 to Robins; 4,378,213 to Severy; 5,066,743 and 4,979,993 to Okamoto et al.; 5,262,200 to Puder et al.; 4,012,402 and 3,903,055 to Buck; and 3,940,362 to Overhults discloses cyanoacrylate monomers polymerized by the addition of various initiators. The compositions are however directed to catalyzing reactions which only require minor stimulation or initiation to occur. U.S. Pat. No. 5,079,098 to Liu also addresses the addition of initiators to cyanoacrylates, but only for the purpose of promoting increased bonding.

U.S. Pat. No. 5,928,611 to Leung broadly discloses 1,1-disubstituted ethylene monomers having a large number of possible substituent groups. The disclosure focuses on alpha cyanoacrylates, with alternative representation of ester cyanoacrylates having an organic radical substituent. However, the disclosure does not specify particular properties, such as absorbability, possessed by particular cyanoacrylates. The disclosure does not indicate which initiators work well with which cyanoacrylates. Not all cyanoacrylates work well with all initiators, because cyanoacrylates and initiators are specific in their polymerization interaction. The disclosure also does not disclose absorption rates, or the effect of the selection of initiators on the properties possessed by cyanoacrylates or polymerization products thereof.

U.S. Pat. No. 3,995,641 to Kronenthal et al. discloses absorbable carbalkoxyalkyl 2-cyanoacrylates. The disclosure does not discuss the use of initiators, but rather indicates that blood and other body fluids polymerize the monomers. The disclosure also does not address the effect of the selection of initiators on the properties possessed by cyanoacrylates or polymerization products thereof.

Absorbable adhesives have additional benefits over non-absorbable adhesives under some circumstances, particularly for some medical applications. However, some absorbable cyanoacrylate adhesive compositions have particularly slow reaction kinetics which reduce their practical value as surgical adhesives. Therefore, there is still a need for an adhesive composition that combines absorbability and a rapid cure rate sufficient for medical applications.

SUMMARY OF THE INVENTION

The present invention is based on a subclass of cyanoacrylates, alkyl ester cyanoacrylates, that possess exceptional adhesive characteristics and additionally are minimally toxic to non-toxic as well as absorbable by living organisms. Benefits of biocompatible adhesives of the invention include ease and rapidity of application, which may be accompanied by inhibition of microbial growth, and lower cost than sutures or staples. The present invention provides a method of treating living tissue, comprising applying to living tissue a biocompatible adhesive composition comprising at least one alkyl ester cyanoacrylate monomer and a polymerization initiator or accelerator, wherein the polymerization initiator or accelerator is a quaternary amine. The combination of an alkyl ester cyanoacrylate and a quaternary amine provides desirable reaction kinetics coupled with absorbability.

The present invention also provides a kit, comprising a saleable package comprising a first container that contains at least one alkyl ester cyanoacrylate monomer; and a polymerization initiator or accelerator, wherein the polymerization initiator or accelerator is a quaternary amine.

The present invention also provides a method of treating living tissue, comprising applying to living tissue a biocompatible adhesive composition comprising a polymerization initiator or accelerator and at least one member selected from the group consisting of butyl lactoyl cyanoacrylate monomer and butyl glycoloyl cyanoacrylate monomer.

The present invention also provides a method of treating living tissue, comprising determining a desired rate at which an adhesive polymer is absorbed; selecting a suitable combination of monomer and polymerization initiator or accelerator to provide the desired absorption rate; and applying to living tissue the polymerization initiator or accelerator and monomer to form an absorbable adhesive polymer.

Absorbable cyanoacrylates have broad application for closure and hemostatic sealing of wounds and the like in various living tissue, including but not limited to internal organs and blood vessels. Due to their biodegradability, these absorbable formulations can be applied on the interior or exterior of blood vessels and various organs and other tissue.

Adhesives of the present invention are biocompatible with living tissue, may be applied in vivo to living tissue, and may be applied internally or externally in or on living tissue.

In embodiments, the present invention provides at least one alkyl ester cyanoacrylate monomer having the formula

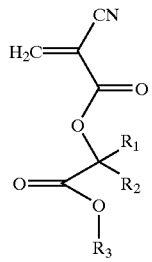

wherein $R_1$ and $R_2$ are independently H, a straight, branched or cyclic alkyl group, or are combined together in a cyclic alkyl group, and $R_3$ is a straight, branched or cyclic alkyl group.

The present invention also provides for the use with the monomers of quaternary amine polymerization initiators or accelerators such as quaternary amines having the formula

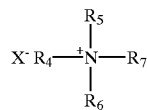

wherein $R_4$, $R_5$, $R_6$ and $R_7$ are each independently H or a substituted or unsubstituted straight, branched or cyclic alkyl group; a substituted or unsubstituted aromatic ring; a substituted or unsubstituted aralkyl group; or a substituted or unsubstituted alkyl or aromatic group which may include one or more hetero atom functionalities such as oxygen, sulfur, nitrogen, etc.; and $X^-$ is an anion such as a halide, for example chloride, bromide, or fluoride, or hydroxyl; suitable quaternary amine initiators include but are not limited to domiphen bromide, butyrylcholine chloride, benzalkonium bromide and acetyl choline chloride.

DETAILED DESCRIPTION OF PREFERRED EMBODIMENTS

The present invention provides a method of treating living tissue, comprising applying to living tissue a biocompatible adhesive composition comprising at least one alkyl ester cyanoacrylate monomer and a polymerization initiator or accelerator, wherein the polymerization initiator or accelerator is a quaternary amine.

For the purposes of this invention, the terms "absorbable" or "absorbable adhesive" mean capable of being absorbed, degraded or biodegraded, either fully or partially, by animal (including human) tissue after application of the adhesive.

For the purposes of this invention, the term "substantially absorbed" means at least 90% absorbed.

For the purposes of this invention, the term "biocompatible" refers to a material being suited for and meeting the requirements of a medical device, used for either long or short term implants or for non-implantable applications, such that when implanted or applied in an intended location, the material serves the intended finction for the required amount of time without causing an unacceptable response. Long term implants are defined as items implanted for more than 30 days.

Preferred monomer compositions of the present invention, and polymers formed therefrom, are useful as tissue adhesives, sealants for preventing bleeding or for covering open wounds, and in other biomedical applications. They find uses in, for example, preventing body fluid leakage, tissue approximation, apposing surgically incised or traumatically lacerated tissues; retarding blood flow from wounds; drug delivery; dressing bums; dressing skin or other superficial or deep tissue surface wounds (such as abrasions, chaffed or raw skin, and/or stomatitis); and aiding repair and regrowth of living tissue. Monomer compositions of the present invention, and polymers formed therefrom, have broad application for sealing wounds in various living tissue, internal organs and blood vessels, and can be applied, for example, on the interior or exterior of blood vessels and various organs or tissues. Monomer compositions of the present invention, and polymers formed therefrom, are also useful in industrial and home applications, for example in bonding rubbers, plastics, wood, composites, fabrics, and other natural and synthetic materials.

Monomers that may be used in this invention are readily polymerizable, e.g. anionically polymerizable or free radical polymerizable, or polymerizable by zwitterions or ion pairs to form polymers. Some such monomers are disclosed in, for example, U.S. Pat. No. 5,328,687 to Leung, et al., which is hereby incorporated in its entirety by reference herein.

Alkyl ester cyanoacrylates can be prepared according to the procedure described in U.S. Pat. No. 3,995,641 to Kronenthal et al., which is hereby incorporated by reference herein. In the Kronenthal et al. method, such cyanoacrylate monomers are prepared by reacting an alkyl ester of an alpha-cyanoacrylic acid with a cyclic 1,3-diene to form a Diels-Alder adduct which is then subjected to alkaline hydrolysis followed by acidification to form the corresponding alpha-cyanoacrylic acid adduct. The alpha-cyanoacrylic acid adduct is preferably esterified by an alkyl bromoacetate to yield the corresponding carbalkoxymethyl alpha-cyanoacrylate adduct. Alternatively, the alpha-cyanoacrylic acid adduct may be converted to the alpha-cyanoacrylyl halide adduct by reaction with thionyl chloride. The alpha-cyanoacrylyl halide adduct is then reacted with an alkyl hydroxyacetate or a methyl substituted alkyl hydroxyacetate to yield the corresponding carbalkoxymethyl alpha-cyanoacrylate adduct or carbalkoxy alkyl alpha-cyanoacrylate adduct, respectively. The cyclic 1,3-diene blocking group is finally removed and the carbalkoxy methyl alpha-cyanoacrylate adduct or the carbalkoxy alkyl alpha-cyanoacrylate adduct is converted into the corresponding carbalkoxy alkyl alpha-cyanoacrylate by heating the adduct in the presence of a slight deficit of maleic anhydride.

Alkyl ester cyanoacylates can also be prepared through the Knoevenagel reaction of an alkyl cyanoacetate, or an alkyl ester cyanoacetate, with paraformaldehyde. This leads to a cyanoacrylate oligomer. Subsequent thermal cracking of the oligomer results in the formation of a cyanoacrylate monomer. After further distillation, a cyanoacrylate monomer with high purity (greater than 95.0%, preferably greater than 99.0%, and more preferably greater than 99.8%), may be obtained.

Monomers prepared with low moisture content and essentially free of impurities (e.g., surgical grade) are preferred for biomedical use. Monomers utilized for industrial purposes need not be as pure.

Preferred alkyl ester cyanoacrylate monomers have the formula

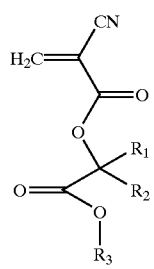

wherein $R_1$ and $R_2$ are, independently H, a straight, branched or cyclic alkyl, or are combined together in a cyclic alkyl group, and $R_3$ is a straight, branched or cyclic alkyl group. Preferably, $R_1$ is H or a $C_1$, $C_2$ or $C_3$ alkyl group, such as methyl or ethyl; $R_2$ is H or a $C_1$, $C_2$ or $C_3$ alkyl group, such as methyl or ethyl; and $R_3$ is a $C_1$–$C_{16}$ alkyl group, more preferably a $C_1$–$C_{10}$ alkyl group, such as methyl, ethyl, propyl, butyl, pentyl, hexyl, heptyl, octyl, nonyl or decyl, and even more preferably a $C_2$, $C_3$ or $C_4$ alkyl group.

Examples of preferred alkyl ester cyanoacrylates include, but are not limited to, butyl lactoyl cyanoacrylate (BLCA), butyl glycoloyl cyanoacrylate (BGCA), ethyl lactoyl cyanoacrylate (ELCA), and ethyl glycoloyl cyanoacrylate (EGCA). BLCA may be represented by formula (I) above, wherein $R_1$ is H, $R_2$ is methyl and $R_3$ is butyl. BGCA may be represented by formula (I) above, wherein $R_1$ is H, $R_2$ is H and $R_3$ is butyl. ELCA may be represented by formula (I) above, wherein $R_1$ is H, $R_2$ is methyl and $R_3$ is ethyl. EGCA may be represented by formula (I) above, wherein $R_1$ is H, $R_2$ is H and $R_3$ is ethyl. Other cyanoacrylates useful in the present invention are disclosed in U.S. Pat. No. 3,995,641 to Kronenthal et al., the entire disclosure of which is hereby incorporated by reference.

Alkyl ester cyanoacrylates are particularly useful for medical applications because of their absorbability by living tissue and associated fluids. According to the present invention, 100% of the polymerized and applied cyanoacrylate may be absorbed in a period of less than 2 years, preferably approximately 2–24 months, more preferably 3–18 months, and most preferably 6–12 months after application of the adhesive to living tissue.

The absorption rate of the polymerized monomer is affected by several factors including the character of the composition and the quantity of adhesive applied. For example, regulating the pH of an immediate in vivo environment of a biocompatible composition may aid in regulating polymer degradation, as disclosed in U.S. patent application Ser. No. 08/714,288, filed Sep. 18, 1996, the entire disclosure of which is hereby incorporated by reference.

The selection of monomer may affect the absorption rate of the resultant polymer, as well as the polymerization rate of the monomer. For example, without being bound by theory, it is believed that the more hygroscopic the initiator, the more rapid will be the degradation of the polymer. Two or more different monomers that have varied absorption and/or polymerization rates may be used in combination to give a greater degree of control over the absorption rate of the resultant polymer, as well as the polymerization rate of the monomer. Thus, an important aspect of embodiments of the invention lies in the selection of the monomer and initiator to control within relatively narrow and predictable ranges both the polymerization and absorption rates.

Alkyl ester cyanoacrylate monomers may react slowly due to relatively large pendant side groups, apparently limiting their applicability as surgical adhesives. By themselves, alkyl ester cyanoacrylates cure in several hours, or in some cases do not fully cure at all. To overcome problems associated with slow polymerization of the monomers, a compatible agent which initiates or accelerates polymerization of the alkyl ester cyanoacrylate monomer, may be used with the monomer composition. Initiators and accelerators particularly suitable for use with alkyl ester cyanoacrylates provide a fast cure rate while retaining the absorbable properties of the adhesive. Alkyl ester cyanoacrylates stimulated to cure by a suitable initiator or accelerator may be made to cure in as short as a few seconds to a few minutes. The cure rate may be closely controlled by selection of an amount or concentration of initiator or accelerator added to the cyanoacrylate and may thus be readily controlled by one skilled in the art in light of the present disclosure. A suitable initiator provides a consistent controllable complete polymerization of the monomer so that the polymerization of the monomer can be made to occur in the time desired for the particular application. Quaternary amine initiators or accelerators are particularly desirable with alkyl ester cyanoacylate monomers for such reasons.

The initiator or accelerator may be in the form of a solid, such as a powder or a solid film, or in the form of a liquid, such as a viscous or paste-like material. The initiator or accelerator may also include a variety of additives, such as surfactants or emulsifiers. Preferably, the initiator or accelerator is soluble in the monomer composition, and/or comprises or is accompanied by at least one surfactant which, in embodiments, helps the initiator or accelerator co-elute with the monomer composition. In embodiments, the surfactant may help disperse the initiator or accelerator in the monomer composition.

The initiator or accelerator may be applied to tissue before the monomer composition, or may be applied directly to the monomer composition once the monomer composition is applied to tissue. In embodiments, the initiator or accelerator may be combined with the monomer composition just prior to applying the composition to tissue.

The selection of an initiator or accelerator may additionally affect the rate at which the polymerized monomer is absorbed by living tissue. Therefore, the most suitable initiators or accelerators are those that polymerize the monomer at a rate suitable for medical applications while providing a polymer that is substantially absorbed in less than two years. Preferable initiators are those that absorb water as the absorption of water encourages the degradation of the polymer. However, since not all initiators absorb water, and initiators that do absorb water do so at different rates, the selection of an initiator based on this property also provides for a degree of control over the degradation of the polymer. For the purposes of this invention, the phrase "suitable for medical application(s)" means that the initiator or accelerator polymerizes the monomer in less than 3 minutes, preferably in less than 2.5 minutes, more preferably in less than 1 minute, and often in less than 45 seconds. Preferably, a suitable initiator or accelerator and a suitable monomer are selected to provide a polymer that is substantially absorbed by a living organism in 2–24 months, more preferably 3–18 months, and most preferably 6–12 months after application of the adhesive to living tissue.

The present invention provides a method of treating living tissue, comprising selecting an alkyl ester cyanoacrylate monomer for treatment of the tissue; determining a desired rate at which an adhesive polymer is absorbed; selecting a suitable polymerization initiator or accelerator for the monomer on the basis of the rate; and applying to living tissue the polymerization initiator or accelerator and said monomer to form an absorbable adhesive polymer. A suitable initiator or accelerator in a suitable quantity can be selected in light of the present disclosure, in combination with the selection of monomer, to produce a polymer with a desired absorption rate. A screening process utilizing routine experimentation may be used to identify combinations of monomers and initiators or accelerators that possess the desired reaction kinetics and produce a polymer that is absorbed in vivo in the desired period of time. Particularly beneficial initiators or accelerators, as well as monomers, are identified by the present disclosure. Therefore, for example, a butyl lactoyl cyanoacrylate monomer may be polymerized with, for example, domiphen bromide to test the polymerization rate. The quantity, or type, of initiator or accelerator or monomer may be adjusted if the desired polymerization rate is not achieved. Further, the polymer may be tested by in vivo application on animal (including human) tissue to determine absorption rates.

Depending, for example, on the necessary healing time for a wound, a corresponding absorption rate may be desired. Since healing times vary in different organisms and different tissues, the ability to control the absorption rate of the adhesive is beneficial to ensure that the adhesive polymer lasts long enough to provide time for the wound to heal, but absorbs within a reasonable time, preferably within 2 years from application of the adhesive to living tissue.

In preferred embodiments, the present invention provides for the use of quaternary amine polymerization initiators or accelerators such as quaternary amines having the formula

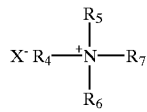

wherein $R_4$, $R_5$, $R_6$ and $R_7$ are each independently H or a substituted or unsubstituted straight, branched or cyclic alkyl group; a substituted or unsubstituted aromatic ring; a substituted or unsubstituted aralkyl group; or a substituted or unsubstituted alkyl or aromatic group which may include one or more hetero atom functionalities such as oxygen, sulfur, nitrogen, etc.; and $X^-$ is an anion such as a halide, for example chloride, bromide, or fluoride, or hydroxyl. In preferred embodiments, at least one of $R_4$, $R_5$, $R_6$ and $R_7$ includes an aromatic group and/or a hetero atom functionality such as an ether or ester linkage or corresponding linkages where the hetero atom is sulfur or nitrogen. Preferred quaternary amine initiators are selected from the group consisting of domiphen bromide, butyrylcholine chloride, benzalkonium bromide and acetyl choline chloride.

Domiphen bromide may be represented by the following formula:

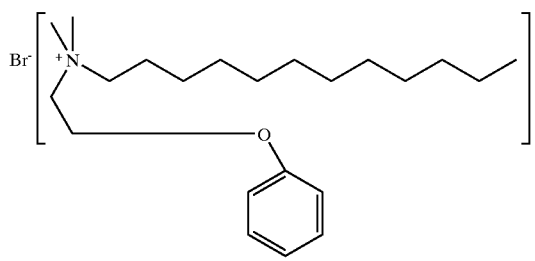

Butyrylcholine chloride may be represented by the following formula:

Initiators or accelerators, such as quaternary amines mentioned above, are preferably used in the present invention, but other initiators or accelerators may also be selected by one of ordinary skill in the art without undue experimentation. Such suitable initiators or accelerators may include, but are not limited to, detergent compositions; surfactants: e.g., nonionic surfactants such as polysorbate 20 (e.g., Tween 20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

Specific compositions of the invention may have various combinations of alkyl ester cyanoacrylates and thickeners, plasticizers, colorants, preservatives, heat dissipating agents, stabilizing agents and the like, which will be described in more detail below. Preferably, a composition of this invention has from 65 to 99.9 weight % of an alkyl ester cyanoacrylate and is promoted to polymerize by 0.005 to 10 weight % of an initiator or accelerator. More preferably, a composition of this invention has from 80 to 99.9 weight % of an alkyl ester cyanoacrylate and is promoted to polymerize by 0.02 to 5 weight % of an initiator or accelerator. Even more preferably, a composition of this invention has 85 to 99.9 weight % of an alkyl ester cyanoacrylate, such as butyl lactoyl cyanoacrylate, and is promoted to polymerize by 0.05 to 3 weight % of an initiator or accelerator, such as domiphen bromide. Compositions of this invention may also include 0 to 25, more preferably 0 to 10, for example 0 to 5 weight % based on a total weight of the composition of at least one of the following: thickeners, plasticizers, colorants, preservatives, heat dissipating agents, stabilizing agents and the like. Of course, other compositions based on other proportions and/or components can readily be prepared according to embodiments of the present invention in light of the present disclosure.

Compositions of the present invention may be utilized in conjunction with other sealing means. For example, an adhesive may be applied to a wound that has been closed using surgical suture, tape, or staples. Adhesives of the present invention may also be used in conjunction with other sealing means, such as means identified in U.S. Pat. No. 6,014,714, the entire disclosure of which is incorporated herein by reference.

Compositions of the present invention may be applied in single or multiple applications. The adhesives may be applied in a first layer, and after the first layer is allowed to fully or partially polymerize, a subsequent layer may be added. Such a process may be conducted numerous times, depending on the size of the wound and the amount of adhesive applied in each application.

The monomeric composition may be packaged in any type of suitable container fabricated from materials including, but not limited to, glass, plastic, metal packages, and film-formed packages. Suitable containers preferably include those into which the compositions may be dispensed and sterilized without unacceptable damage to, or degradation of, the container or the components of the monomer composition. Post-halogenated, such as fluourinated, polymeric barrier layers on at least the monomer-contacting surfaces of the container provide a superior shelf-life for monomer compositions, as disclosed in U.S. patent application Ser. No. 09/430,289, filed Oct. 29, 1999, the entire disclosure of which is hereby incorporated by reference. Glass is especially preferred when sterilization is achieved with dry heat because of the lack of stability of many plastics at temperatures used for dry heat sterilization (typically at least 160° C.). Examples of types of containers include, but are not limited to, ampoules, vials, syringes, pipettes, and the like.

The present invention also provides a saleable kit for delivering an absorbable cyanoacrylate adhesive to tissue. The kit comprises a saleable package comprising a first container that contains at least one alkyl ester cyanoacrylate monomer; and a polymerization initiator or accelerator, wherein the polymerization initiator or accelerator is a quaternary amine. The kit may comprise a second container containing the quaternary amine as described herein. Or, the first container could have the initiator or accelerator in or on it as long as the initiator or accelerator is not in contact with the monomer prior to the desired use. The initiator or accelerator is selected so that it functions in conjunction with the co-packaged polymerizable monomer composition to initiate polymerization of the monomer or modify (e.g., accelerate) the rate of polymerization for the monomer to form a polymeric adhesive. The proper combination of initiator or accelerator and polymerizable monomer can be determined by one of skill in the art without undue experimentation in light of the present disclosure. The kit may also include a brush, swab or sponge to assist in applying the composition to living tissue. The kit is also preferably sterilized; however, the containers and components may be sterilized separately or together. Preferably, kits and the kit components (including compositions) of the present invention have a sterility level in the range of $10^{-3}$ to $10^{-6}$ Sterility Assurance Level (SAL) and are sterile for surgical purposes. Various designs of such kits are disclosed, for example, in U.S. patent application Ser. No. 09/385,030, filed Aug. 30, 1999, the entire disclosure of which is herein incorporated by reference. The sterilization may be accomplished by techniques known to the skilled artisan, and is preferably accomplished by methods including, but not limited to, chemical, physical, and irradiation methods. Examples of physical methods include, but are not limited to, sterile fill, filtration, sterilization by heat (dry or moist) and retort canning. Examples of irradiation methods include, but are not limited to, gamma irradiation, electron beam irradiation, and microwave irradiation. Preferred methods are dry and moist heat sterilization and electron beam irradiation. In embodiments where a composition is to be used for medical applications, the sterilized composition should show low levels of toxicity to living tissue during its useable life.

In embodiments of the present invention, any suitable applicator may be used to apply the adhesive composition to a substrate. For example, the applicator may include an applicator body, which is formed generally in the shape of a tube having a closed end, an open end, and a hollow interior lumen, which holds a crushable or frangible ampoule. The applicator and its related packaging may be designed as a single-use applicator or as a multi-use applicator. Suitable multi-use applicators are disclosed, for example, in U.S. patent application Ser. No. 09/385,030, filed Aug. 30, 1999, the entire disclosure of which is incorporated herein by reference.

In embodiments of the invention, the applicator may comprise elements other than an applicator body and an ampoule. For example, an applicator tip may be provided on the open end of the applicator. The applicator tip material may be porous, absorbent, or adsorbent in nature to enhance and facilitate application of the composition within the ampoule. Suitable designs for applicators and applicator tips that may be used according to the present invention are disclosed in, for example, U.S. Pat. No. 5,928,611 to Leung and U.S. patent applications Ser. Nos. 09/069,979, filed Apr. 30, 1998, 09/069,875, filed Apr. 30, 1998, 09/479,059, filed Jan. 7, 2000, and 09/479,060, filed Jan. 7, 2000, the entire disclosures of which are incorporated herein by reference.

In embodiments of the present invention, an applicator may contain the initiator or accelerator on a surface portion of the applicator or applicator tip, or on the entire surface of the applicator tip, including the interior and the exterior of the tip. When the initiator or accelerator is contained in or on an applicator tip, the initiator or accelerator may be applied to the surface of the applicator tip or may be impregnated or incorporated into the matrix or internal portions of the applicator tip. Additionally, the initiator or accelerator may be incorporated into the applicator tip, for example, during the fabrication of the tip.

In other embodiments, the initiator or accelerator may be coated on an interior surface of the applicator body and/or on an exterior surface of an ampoule or other container disposed within the applicator body, may be placed in the applicator body in the form of a second frangible vial or ampoule and/or may be otherwise contained within the applicator body, so long as a non-contacting relationship between the polymerizable monomer composition and the initiator or accelerator is maintained until use of the adhesive.

Various designs of applicators and methods for incorporating the initiator or accelerator into the applicator are disclosed in U.S. Pat. No. 5,928,611 to Leung and U.S. patent applications Ser. Nos. 09/069,979, filed Apr. 30, 1998, 09/069,875, filed Apr. 30, 1998, 09/145,200, filed Sep. 1, 1998, the entire disclosures of which are incorporated herein by reference.

Preservatives useful in compositions of this invention may be anti-microbial agents. In embodiments, a preservative may be selected from among preservatives including, but not limited to, parabens and cresols. For example, suitable parabens include, but are not limited to, alkyl parabens and salts thereof, such as methylparaben, methylparaben sodium, ethylparaben, propylparaben, propylparaben sodium, butylparaben, and the like. Suitable cresols include, but are not limited to, cresol, chlorocresol, and the like. The preservative may also be selected from other known agents including, but not limited to, hydroquinone, pyrocatechol, resorcinol, 4-n-hexyl resorcinol, captan (i.e., 3a,4,7,7a-tetrahydro-2-((trichloromethyl)thio)-1H-isoindole-1,3(2H)-dione), benzoic acid, benzyl alcohol, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, phenylmercuric compounds such as phenylmercuric borate, phenylmercuric nitrate and phenylmercuric acetate, formaldehyde, and formaldehyde generators such as the preservatives Germall II® and Germall 115® (imidazolidinyl urea, available from Sutton Laboratories, Charthan, N.J.). Other suitable preservatives are disclosed in U.S. patent application Ser. No. 09/430,180, filed Oct. 29, 1999, the entire disclosure of which is hereby incorporated by reference. In embodiments, mixtures of two or more preservatives may also be used.

Monomer compositions of the invention may also include a heat dissipating agent. Heat dissipating agents include liquids or solids that may be soluble or insoluble in the monomer. The liquids may be volatile and may evaporate during polymerization, thereby releasing heat from the composition. Suitable heat dissipating agents may be found in U.S. Pat. No. 6,010,714 to Leung et al., the entire disclosure of which is incorporated herein.

The composition may also optionally include at least one plasticizing agent that imparts flexibility to the polymer formed from the monomer. The plasticizing agent preferably contains little or no moisture and should not significantly affect the stability or polymerization of the monomer. Such plasticizers are useful in polymerized compositions to be used for closure or covering of wounds, incisions, abrasions, sores or other applications where flexibility of the adhesive is desirable. Some thickeners, such as poly-2-ethylhexylcyanoacrylate, may also impart flexibility to the polymer.

Examples of suitable plasticizers include acetyl tributyl citrate, dimethyl sebacate, triethyl phosphate, tri(2-ethylhexyl)phosphate, tri(p-cresyl) phosphate, glyceryl triacetate, glyceryl tributyrate, diethyl sebacate, dioctyl adipate, isopropyl myristate, butyl stearate, lauric acid, trioctyl trimellitate, dioctyl glutarate, polydimethylsiloxane, and mixtures thereof. Preferred plasticizers are tributyl citrate and acetyl tributyl citrate. In embodiments, suitable plasticizers include polymeric plasticizers, such as polyethylene glycol (PEG) esters and capped PEG esters or ethers, polyester glutarates and polyester adipates.

The addition of plasticizing agents in amounts ranging from about 0.5 wt. % to about 25 wt. %, or from about 1 wt. % to about 20 wt. %, or from about 3 wt. % to about 15 wt. % or from about 5 wt. % to about 7 wt. % provides increased elongation and toughness of the polymerized monomer over polymerized monomers not having plasticizing agents.

The composition may also include at least one thickening agent. Suitable thickening agents include, for example, polycyanoacrylates, polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

The composition may also optionally include at least one thixotropic agent. Suitable thixotropic agents are known to the skilled artisan and include, but are not limited to, silica gels such as those treated with a silyl isocyanate. Examples of suitable thixotropic agents are disclosed in, for example, U.S. Pat. No. 4,720,513, the disclosure of which is hereby incorporated in its entirety.

The composition may also optionally include at least one natural or synthetic rubber to impart impact resistance, which is preferable especially for industrial compositions of the present invention. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties.

The composition may also optionally include at least one anionic vapor phase stabilizer and/or at least one anionic liquid phase stabilizer. These stabilizing agents inhibit premature polymerization. Such stabilizing agents may also include mixtures of anionic stabilizing agents and radical stabilizing agents. Any mixture of stabilizers is included as long as the mixture does not adversely affect the desired polymerization and absorption of the monomer. Suitable stabilizing agents are disclosed in, for example, U.S. patent application Ser. No. 09/099,457, filed Jun. 18, 1998, the entire disclosure of which is hereby incorporated by reference.

Anionic vapor phase stabilizers may be selected from among known stabilizers, including, but not limited to, sulfur dioxide, boron trifluoride, and hydrogen fluoride. The amount of anionic vapor phase stabilizer that is added to the monomer composition depends on the identity of the liquid phase stabilizer(s) chosen in combination with it, the monomer to be stabilized, as well as the packaging material to be used for the composition. Preferably, each anionic vapor phase stabilizer is added to give a concentration of less than 200 parts per million (ppm). In preferred embodiments, each anionic vapor phase stabilizer is present from about 1 to 200 ppm, more preferably from about 10 to 75 ppm, even more preferably from about 10 to 50 ppm, and most preferably from 10 to 20 ppm. The amount to be used may be determined by one of ordinary skill in the art using known techniques without undue experimentation.

In embodiments, the vapor phase comprises, among other things, an anionic stabilizer that is sulfur dioxide. In embodiments, the vapor phase comprises, among other things, a stabilizer that is boron trifluoride or hydrogen fluoride. A combination of sulfur dioxide and boron trifluoride or hydrogen fluoride is preferable in some embodiments.

In embodiments, the liquid phase anionic stabilizer is a very strong acid. As used herein, a very strong acid is an acid that has an aqueous $pK_a$ of less than 1.0. Suitable very strong acidic stabilizing agents include, but are not limited to, very strong mineral and/or oxygenated acids. Examples of such very strong acids include, but are not limited to, sulfuric acid ($pK_a$–3.0), perchloric acid ($pK_a$–5), hydrochloric acid ($pK_a$–7.0), hydrobromic acid ($pK_a$–9), fluorosulfonic acid ($pK_a$<–10), chlorosulfonic acid ($pK_a$–10). In embodiments, the very strong acid liquid phase anionic stabilizer is added to give a final concentration of 1 to 200 ppm. Preferably, the very strong acid liquid phase anionic stabilizer is present in a concentration of from about 5 to 80 ppm, more preferably 10 to 40 ppm. The amount of very strong acid liquid phase anionic stabilizer to be used may be determined by one of ordinary skill in the art without undue experimentation.

Preferably, the very strong acid liquid phase anionic stabilizer is sulfuric acid, perchloric acid, or chlorosulfonic acid. More preferably, the very strong acid liquid phase anionic stabilizer is sulfuric acid.

In embodiments, sulfur dioxide is used as a vapor phase anionic stabilizer and sulfuric acid is used as a liquid phase anionic stabilizer.

The composition may also optionally include at least one other anionic stabilizing agent that inhibits polymerization. These agents are herein referred to as secondary anionic active agents to contrast them with the strong or very strong liquid phase anionic stabilizers, which are referred to hereinbelow as "primary" anionic stabilizers. The secondary anionic active agents can be included in the compositions to adjust the cure speed of the adhesive composition, for example.

The secondary anionic active agent would normally be an acid with a higher $pK_a$ than the primary anionic stabilizing agent and may be provided to more precisely control the cure speed and stability of the adhesive, as well as the molecular weight of the cured adhesive. Any mixture of primary anionic stabilizers and secondary active agents is included as long as the chemistry of the composition is not compromised and the mixture does not significantly inhibit the desired polymerization of the composition. Furthermore, the mixture should not, in medical adhesive compositions, show unacceptable levels of toxicity.

Suitable secondary anionic active agents include those having aqueous $pK_a$ ionization constants ranging from 2 to 8, preferably from 2 to 6, and most preferably from 2 to 5. Examples of such suitable secondary anionic stabilizing agents include, but are not limited to, phosphoric acid ($pK_a 2.2$), organic acids, such as acetic acid ($pK.4.8$), benzoic acid ($pK_a 4.2$), chloroacetic acid ($pK_a 2.9$), cyanoacetic acid, and mixtures thereof. Preferably these secondary anionic stabilizing agents are organic acids, such as acetic acid or benzoic acid. In embodiments, the amount of acetic acid and/or benzoic acid is about 25–500 ppm. The concentration of acetic acid is typically 50–400 ppm, preferably 75–300 ppm, and more preferably 100–200 ppm. When using a stronger acid such as phosphoric acid, a concentration of 20–100 ppm, preferably 30–80 ppm, and more preferably 40–60 ppm may be utilized.

Combinations of at least one vapor phase stabilizer and at least one liquid phase anionic stabilizer are preferred. For example, combinations of sulfur dioxide and sulfuric acid, sulfur dioxide and perchloric acid, sulfur dioxide and chlorosulfonic acid, boron trifluoride and sulfuric acid, boron trifluoride and perchloric acid, boron trifluoride and chlorosulfonic acid, boron trifluoride and methanesulfonic acid, hydrogen fluoride and sulfuric acid, hydrogen fluoride and perchloric acid, hydrogen fluoride and chlorosulfonic acid, and hydrogen fluoride and methanesulfonic acid may be used. A combination of boron trifluoride, sulfur dioxide, and sulfuric acid may also be used, among other combinations. The two types of anionic stabilizers are chosen in conjunction such that the stabilizers are compatible with the chosen adhesive composition and each other stabilizer, as well as with the packaging material and the equipment used to make and package the composition. In other words, the combination of vapor phase stabilizer(s), liquid phase stabilizer(s), and monomer should be such that a stabilized, substantially unpolymerized adhesive composition is present after packaging.

Compositions of the present invention have reduced toxicity compared to other cyanoacrylates, such as methyl cyanoacrylate and ethyl cyanoacrylate. However, medical compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites; ammonium sulfite salts; amines; amides; imides; nitriles; carbamates; alcohols; mercaptans; proteins; mixtures of amines, amides, and proteins; active methylene compounds such as cyclic ketones and compounds having a b-dicarbonyl group; and heterocyclic ring compounds free of a carbonyl group and containing an NH group, with the ring made up of nitrogen or carbon atoms, the ring being unsaturated or, when fused to a phenyl group, being unsaturated or saturated, and the NH group being bonded to a carbon or a nitrogen atom, which atom is directly bonded by a double bond to another carbon or nitrogen atom.

Other examples of formaldehyde level reducing compounds and compositions are exemplified by U.S. Pat. Nos. 6,010,714; 5,624,669; 5,582,834; 5,575,997, the entire disclosures of which are hereby incorporated by reference.

To improve the cohesive strength of adhesives formed from the compositions of this invention, difunctional monomeric cross-linking agents may be added to the monomer compositions of this invention. Such crosslinking agents are known. U.S. Pat. No. 3,940,362 to Overhults, which is hereby incorporated in its entirety by reference, discloses such cross-linking agents. Examples of suitable crosslinking agents include alkyl bis(2-cyanoacrylates), triallyl isocyanurates, alkylene diacrylates, alkylene dimethacrylates, trimethylol propane triacrylate, and alkyl bis(2-cyanoacrylates). In accordance with the present disclosure, a catalytic amount of an amine activated free radical initiator, accelerator or rate modifier may be added to initiate polymerization or to modify the rate of polymerization of the cyanoacrylate monomer/crosslinking agent blend.

The compositions of this invention may further contain fibrous reinforcement and colorants such as dyes, pigments, and pigment dyes. Examples of suitable fibrous reinforcement include PGA microfibrils, collagen microfibrils, cellulosic microfibrils, and olefinic microfibrils. Examples of suitable colorants include 1-hydroxy-4-[4-methylphenylamino]-9,10 anthracenedione (D+C violet No. 2); disodium salt of 6-hydroxy-5-[(4-sulfophenyl)axo]-2-naphthalenesulfonic acid (FD+C Yellow No. 6); 9-(o-carboxyphen0yl)-6-hydroxy-2,4,5,7-tetraiodo-3H-xanthen-3-one, disodium salt, monohydrate (FD+C Red No. 3); 2-(1,3-dihydro-3-oxo-5-sulfo-2H-indol-2-ylidene)-2,3-dihydro-3-oxo-1H-indole-5-sulfonic acid disodium salt (FD+C Blue No. 2); and [phthalocyaninato (2-)] copper.

Other modifications to compositions of the present invention are exemplified by U.S. Pat. Nos. 5,624,669; 5,582,834; 5,575,997; 5,514,371; 5,514,372; and 5,259,835; and U.S. patent application Ser. No. 08/714,288, the disclosures of all of which are hereby incorporated in their entirety by reference.

EXAMPLES

The present invention will be further understood by reference to the following non-limiting examples.

Example 1

70 $\mu$l of butyl lactoyl cyanoacrylate are mixed with 2.5 $\mu$moles of domiphen bromide as the monomer is passed through a porous applicator tip. The resulting mixture sets in approximately 40 seconds.

Example 2

36 μl of butyl lactoyl cyanoacrylate are mixed with 0.625 μmoles of butyrylcholine chloride as the monomer is passed through a porous applicator tip. The resulting mixture sets in approximately 60 seconds.

Example 3

A polymer is formed from the initiation of butyl lactoyl cyanoacrylate monomer with domiphen bromide in situ on a polypropylene mesh and placed in a phosphate buffer at 39° C. Samples are rinsed, dried and weighed, and the degradation results of the polymer are shown in the table below, wherein Mn is the number average molecular weight of the sample.

|  | Time (days) | | | | | |
| --- | --- | --- | --- | --- | --- | --- |
|  | 0 | 28 | 56 | 84 | 112 | 140 |
| Mass loss (%) | 0 | 8 | 18 | 31 | 45 | 60 |
| Mn × 1,000 | 84 | 12 | 6.2 | 3.1 | 1.9 | 1.3 |

A polymer is formed from the initiation of butyl lactoyl cyanoacrylate monomer with azobisisobutyronitrile in situ on a polypropylene mesh and placed in a phosphate buffer at 39° C. Samples are rinsed, dried and weighed, and the degradation results of the polymer are shown in the table below, wherein Mn is the number average molecular weight of the sample.

|  | Time (days) | | | | | |
| --- | --- | --- | --- | --- | --- | --- |
|  | 0 | 28 | 56 | 98 | 112 | 140 |
| Mass loss (%) | 0 | 3 | 6 | 9 | 10 | 12 |
| Mn × 1,000 | 28 | 23 | 23 | 21 | — | 20 |

Example 4

An absorbable adhesive polymer is formulated by the combination of:

| Butyl lactoyl cyanoacrylate monomer | 98.2600% (by weight); |
| --- | --- |
| Domiphen bromide | 1.7300% (by weight); |
| H$_2$SO$_4$ | 0.0025% (by weight); and |
| Butylated hydroxyanisole | 0.0075% (by weight). |

While the invention has been described with reference to preferred embodiments, the invention is not limited to the specific examples given, and other embodiments and modifications can be made by those skilled in the art without departing from the spirit and scope of the invention.

What is claimed is:

1. A method of treating living tissue, comprising:
applying to living tissue a biocompatible adhesive composition comprising at least one alkyl ester cyanoacrylate monomer and a polymerization initiator or accelerator, wherein said polymerization initiator or accelerator is a quaternary amine,
wherein said at least one alkyl ester cyanoacrylate monomer has the formula

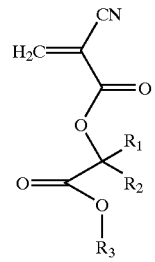

wherein $R_1$ and $R_2$ are independently H, a straight, branched or cyclic alkyl group, or are combined together in a cyclic alkyl group, and $R_3$ is a straight, branched or cyclic alkyl group.

2. The method of claim 1, wherein the polymerization initiator or accelerator is combined with the at least one monomer prior to applying the composition to living tissue.

3. The method of claim 1, wherein the polymerization initiator or accelerator is combined with the at least one monomer after the at least one monomer is applied to living tissue.

4. A The method of claim 1, wherein the at least one monomer is combined with the polymerization initiator or accelerator after the polymerization initiator or accelerator is applied to living tissue.

5. The method of claim 1, wherein $R_1$ is H or a $C_1$–$C_3$ alkyl group; $R_2$ is H or a $C_1$–$C_3$ alkyl group; and $R_3$ is a $C_1$–$C_{16}$ alkyl group.

6. The method of claim 1, wherein $R_3$ is a $C_1$–$C_{10}$ alkyl group.

7. The method of claim 1, wherein $R_3$ is a $C_2$–$C_4$ alkyl group.

8. The method of claim 1, wherein $R_3$ is butyl.

9. The method of claim 1, wherein the at least one alkyl ester cyanoacrylate monomer is butyl lactoyl cyanoacrylate.

10. The method of claim 1, wherein the at least one monomer is butyl glycoloyl cyanoacrylate.

11. The method of claim 1, wherein said polymerization initiator or accelerator has the following formula

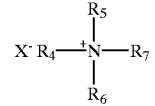

wherein $R_4$, $R_5$, $R_6$ and $R_7$ are each independently H or a substituted or unsubstituted straight, branched or cyclic alkyl group; a substituted or unsubstituted aromatic group; a substituted or unsubstituted aralkyl group; or a substituted or unsubstituted alkyl or aromatic group containing one or more hetero atoms; and X$^-$ is an anion.

12. The method of claim 11, wherein at least one of $R_4$, $R_5$, $R_6$ and $R_7$ comprises at least one member selected from the group consisting of an aromatic ring and a hetero atom-containing linkage.

13. The method of claim 11, wherein X$^-$ is a halogen radical.

14. The method of claim 1, wherein said polymerization initiator or accelerator is at least one member selected from the group consisting of domiphen bromide, butyrylcholine chloride, benzalkonium bromide, and acetyl choline chloride.

15. The method of claim 1, wherein said adhesive composition further comprises at least one component selected from the group consisting of a thickener, a plasticizer, a colorant, a preservative, a heat dissipating agent, an acidic stabilizing agent, and a formaldehyde scavenger.

16. The method of claim 11, wherein said adhesive composition further comprises at least one component selected from the group consisting of a thickener, a plasticizer, a colorant, a preservative, a heat dissipating agent, an acidic stabilizing agent, and a formaldehyde scavenger.

17. The method of claim 1, wherein said adhesive composition further comprises at least one other cyanoacrylate monomer.

18. The method of claim 1, wherein said adhesive composition has a Sterility Assurance Level (SAL) value of $10^{-3}$–$10^{-6}$.

19. The method of claim 1, wherein said at least one monomer is applied in an amount of 65 to 99.9 weight % and said polymerization initiator or accelerator is applied in an amount of 0.005 to 10 weight %, based on a total weight of said composition.

20. The method of claim 1, wherein said at least one monomer is applied in an amount of 80 to 99 weight % and said polymerization initiator or accelerator is applied in an amount of 0.02 to 5 weight %, based on a total weight of said composition.

21. The method of claim 1, wherein said at least one monomer is applied in an amount of 85 to 99 weight % and said polymerization initiator or accelerator is applied in an amount of 0.05 to 3 weight %, based on a total weight of said composition.

22. The method of claim 1, wherein the method is used to close or seal a wound.

23. The method of claim 1, wherein the method is used to close or seal a wound in internal tissue.

24. The method of claim 1, further comprising suturing or stapling said tissue before or after applying said biocompatible adhesive composition to said tissue.

25. The method of claim 1, wherein said tissue is a blood vessel.

26. A kit comprising a saleable package comprising:
a first container that contains a biocompatible adhesive composition comprising at least one alkyl ester cyanoacrylate monomer; and
a polymerization initiator or accelerator, wherein said polymerization initiator or accelerator is a quaternary amine,
wherein said at least one alkyl ester cyanoacrylate monomer has the formula

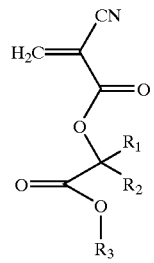

wherein $R_1$ and $R_2$ are independently H, a straight, branched or cyclic alkyl group, or are combined together in a cyclic alkyl group, and $R_3$ is a straight, branched or cyclic alkyl group.

27. The kit of claim 27, wherein said polymerization initiator or accelerator is contained in a second container.

28. The kit of claim 27, wherein said polymerization initiator or accelerator is contained in the first container, but not in contact with said at least one monomer.

29. The kit of claim 27, wherein said at least one monomer is contained in a first frangible ampoule and said polymerization initiator or accelerator is contained in a second frangible ampoule.

30. The kit of claim 27, wherein said polymerization initiator or accelerator is contained in a tip of said first container.

31. The kit of claim 27, further comprising at least one member selected from the group consisting of a brush, swab and sponge.

32. The kit of claim 27, wherein $R_1$ is H or a $C_1$–$C_3$ alkyl group; $R_2$ is H or a $C_1$–$C_3$ alkyl group; and $R_3$ is a $C_1$–$C_{16}$ alkyl group.

33. The kit of claim 27, wherein $R_3$ is a $C_1$–$C_{10}$ alkyl group.

34. The kit of claim 27, wherein $R_3$ is a $C_2$–$C_4$ alkyl group.

35. The kit of claim 27, wherein $R_3$ is butyl.

36. The kit of claim 27, wherein said at least one monomer is butyl lactoyl cyanoacrylate.

37. The kit of claim 27, wherein said at least one monomer is butyl glycoloyl cyanoacrylate.

38. The kit of claim 27, wherein said polymerization initiator or accelerator has the following formula

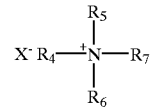

wherein $R_4$, $R_5$, $R_6$ and $R_7$ are each independently H or a substituted or unsubstituted straight, branched or cyclic alkyl group; a substituted or unsubstituted aromatic group; a substituted or unsubstituted aralkyl group; or a substituted or unsubstituted alkyl or aromatic group containing one or more hetero atoms; and $X^-$ is an anion.

39. The kit of claim 38, wherein at least one of $R_4$, $R_5$, $R_6$ and $R_7$ comprises at least one member selected from the group consisting of an aromatic ring and a hetero atom-containing linkage.

40. The kit of claim 38, wherein $X^-$ is a halogen radical.

41. The kit of claim 27, wherein said polymerization initiator or accelerator is at least one member selected from the group consisting of domiphen bromide, butyrylcholine chloride, benzalkonium bromide, and acetyl choline chloride.

42. The kit of claim 27, wherein said adhesive composition further comprises at least one component selected from the group consisting of a thickener, a plasticizer, a colorant, a preservative, a heat dissipating agent, an acidic stabilizing agent, and a formaldehyde scavenger.

43. The kit of claim 38, wherein said adhesive composition further comprises at least one component selected from the group consisting of a thickener, a plasticizer, a colorant, a preservative, a heat dissipating agent, an acidic stabilizing agent, and a formaldehyde scavenger.

44. The kit of claim 27, wherein said adhesive composition further comprises at least one other cyanoacrylate monomer.

45. The kit of claim 27, wherein said adhesive composition has a Sterility Assurance Level (SAL) value of $10^{-3}$–$10^{-6}$.

46. The kit of claim 27, wherein said kit has a Sterility Assurance Level (SAL) value of $10^{-3}$–$10^{-6}$.

47. A method of treating living tissue, comprising:
applying to internal living tissue in a living organism a biocompatible adhesive composition comprising a polymerization initiator or accelerator and at least one monomer selected from the group consisting of butyl lactoyl cyanoacrylate monomer and butyl glycoloyl cyanoacrylate monomer.

48. The method of claim 47, wherein said polymerization initiator or accelerator is a quaternary amine.

49. The method of claim 47, wherein the polymerization initiator or accelerator is combined with said at least one monomer prior to applying the composition to said tissue.

50. The method of claim 47, wherein the polymerization initiator or accelerator is combined with said at least one monomer after said at least one monomer is applied to said tissue.

51. The method of claim 47, wherein said at least one monomer is added to the polymerization initiator or accelerator after the polymerization initiator or accelerator is applied to said tissue.

52. The method of claim 47, wherein said polymerization initiator or accelerator promotes polymerization of said at least one monomer at a rate suitable for medical application and produces a polymer that is absorbed by said living organism in less than 2 years.

53. The method of claim 47, wherein said polymerization initiator or accelerator has the following formula

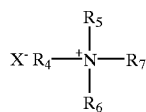

wherein $R_4$, $R_5$, $R_6$ and $R_7$ are each independently H or a substituted or unsubstituted straight, branched or cyclic alkyl group; a substituted or unsubstituted aromatic group; a substituted or unsubstituted aralkyl group; or a substituted or unsubstituted alkyl or aromatic group containing one or more hetero atoms; and $X^-$ is an anion.

54. The method of claim 53, wherein at least one of $R_4$, $R_5$, $R_6$ and $R_7$ comprises at least one member selected from the group consisting of an aromatic ring and a hetero atom-containing linkage.

55. The method of claim 53, wherein $X^-$ is a halogen radical.

56. The method of claim 47, wherein said polymerization initiator or accelerator is at least one member selected from the group consisting of domiphen bromide, butyrylcholine chloride, benzalkonium bromide, and acetyl choline chloride.

57. The method of claim 47, wherein said adhesive composition further comprises at least one component selected from the group consisting of a thickener, a plasticizer, a colorant, a preservative, a heat dissipating agent, an acidic stabilizing agent, and a formaldehyde scavenger.

58. A method of treating living tissue, comprising:
selecting an alkyl ester cyanoacrylate monomer for treatment of said tissue;
determining a desired rate at which an adhesive polymer of said monomer is absorbed;
selecting a suitable polymerization initiator or accelerator for said monomer on the basis of said desired rate; and
applying to living tissue said polymerization initiator or accelerator and said monomer to form an absorbable adhesive polymer on said tissue,
wherein said alkyl ester cyanoacrylate monomer has the formula

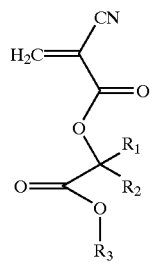

wherein $R_1$ and $R_2$ are independently H, a straight, branched or cyclic alkyl group, or are combined together in a cyclic alkyl group, and $R_3$ is a straight, branched or cyclic alkyl group.

59. The method of claim 58, wherein said alkyl ester cyanoacrylate monomer is at least one member selected from the group consisting of butyl lactoyl cyanoacrylate monomer and butyl glycoloyl cyanoacrylate monomer.

60. The method of claim 58, wherein said polymerization initiator or accelerator is a quaternary amine.

61. The method of claim 58, wherein said polymerization initiator or accelerator has the following formula

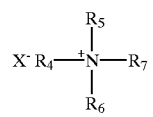

wherein $R_4$, $R_5$, $R_6$ and $R_7$ are each independently H or a substituted or unsubstituted straight, branched or cyclic alkyl group; a substituted or unsubstituted aromatic group; a substituted or unsubstituted aralkyl group; or a substituted or unsubstituted alkyl or aromatic group containing one or more hereto atoms; and $X^-$ is an anion.

62. The method of claim 61, wherein at least one of $R_4$, $R_5$, $R_6$ and $R_7$ comprises at least one member selected from the group consisting of an aromatic ring and a hetero atom-containing linkage.

63. The method of claim 58, wherein said polymerization initiator or accelerator is at least one member selected from the group consisting of domiphen bromide, butyrylcholine chloride, benzalkonium bromide, and acetyl choline chloride.

64. A biocompatible adhesive composition, comprising:
at least one alkyl ester cyanoacrylate monomer; and
a polymerization initiator or accelerator, wherein said polymerization initiator or accelerator is a quaternary amine,
wherein said at least one alkyl ester cyanoacrylate monomer has the formula

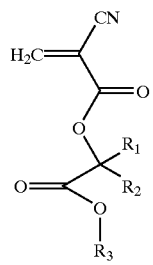

wherein $R_1$ and $R_2$ are independently H, a straight, branched or cyclic alkyl group, or are combined together in a cyclic alkyl group, and $R_3$ is a straight, branched or cyclic alkyl group.

65. The composition of claim 64, wherein said at least one monomer is butyl lactoyl cyanoacrylate.

66. The composition of claim 64, wherein said at least one monomer is butyl glycoloyl cyanoacrylate.

67. The composition of claim 64, wherein said polymerization initiator or accelerator has the formula

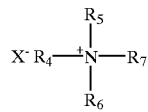

wherein $R_4$, $R_5$, $R_6$ and $R_7$ are each independently H or a substituted or unsubstituted straight, branched or cyclic alkyl group; a substituted or unsubstituted aromatic group; a substituted or unsubstituted aralkyl group; or a substituted or unsubstituted alkyl or aromatic group containing one or more hetero atoms; and $X^-$ is an anion.

68. The composition of claim 67, wherein at least one of $R_4$, $R_5$, $P_6$ and $R_7$ comprises at least one member selected from the group consisting of an aromatic ring and a hetero atom-containing linkage.

69. The composition of claim 64, wherein said polymerization initiator or accelerator is at least one member selected from the group consisting of domiphen bromide, butyrylcholine chloride, benzalkonium bromide, and acetyl choline chloride.

70. A polymerized film formed by curing the composition of claim 64.

71. The method of claim 1, wherein a polymer formed from said biocompatible adhesive composition is absorbed by said living tissue in a period of less than two years after application to the living tissue.

72. The method of claim 1, wherein said polymerization initiator or accelerator polymerizes said at least one alkyl ester cyanoacrylate monomer in less than 3 minutes.

* * * * *